United States Patent
Hufford et al.

(10) Patent No.: US 12,350,112 B2
(45) Date of Patent: Jul. 8, 2025

(54) CREATING SURGICAL ANNOTATIONS USING ANATOMY IDENTIFICATION

(71) Applicant: Asensus Surgical US, Inc., Durham, NC (US)

(72) Inventors: Kevin Andrew Hufford, Cary, NC (US); Lior Alpert, Haifa (IL); Tal Nir, Haifa (IL); Nevo Yokev, Haifa (IL); Dustin Owen Vaughan, Raleigh, NC (US); Caleb T Osborne, Durham, NC (US)

(73) Assignees: Asensus Surgical US, Inc., Durham, NC (US); Asensus Surgical Europe S.à.R.L., Bertrange (LU)

( * ) Notice: Subject to any disclaimer, the term of this patent is extended or adjusted under 35 U.S.C. 154(b) by 0 days.

(21) Appl. No.: 17/679,080

(22) Filed: Feb. 23, 2022

(65) Prior Publication Data

US 2022/0354613 A1 Nov. 10, 2022

Related U.S. Application Data

(60) Provisional application No. 63/152,841, filed on Feb. 23, 2021.

(51) Int. Cl.
*A61B 1/00* (2006.01)
*A61B 90/00* (2016.01)

(52) U.S. Cl.
CPC ........ *A61B 90/361* (2016.02); *A61B 1/00009* (2013.01); *A61B 1/000094* (2022.02); *A61B 1/000095* (2022.02); *A61B 1/000096* (2022.02); *A61B 1/00045* (2013.01)

(58) Field of Classification Search
CPC ............ A61B 1/00045; A61B 1/00009; A61B 1/000094; A61B 1/00095; A61B 1/000096; A61B 90/361; A61B 2090/364; A61B 2090/367; A61B 2090/368; A61B 34/10; A61B 2034/107
See application file for complete search history.

(56) References Cited

U.S. PATENT DOCUMENTS

| | | | |
|---|---|---|---|
| 9,430,706 B1 * | 8/2016 | Peleg | G06V 20/49 |
| 2005/0054910 A1 * | 3/2005 | Tremblay | A61B 34/20 |
| | | | 600/414 |
| 2009/0131793 A1 * | 5/2009 | Stonefield | G01S 7/52084 |
| | | | 600/443 |
| 2015/0287192 A1 * | 10/2015 | Sasaki | H04N 23/56 |
| | | | 382/128 |
| 2016/0148053 A1 * | 5/2016 | Matsuzaki | G06T 7/246 |
| | | | 382/128 |
| 2016/0157710 A1 * | 6/2016 | Tomatsu | A61B 3/14 |
| | | | 351/206 |

(Continued)

*Primary Examiner* — Timothy J Neal
*Assistant Examiner* — William B Chou

(57) ABSTRACT

A system and method allow creation of surgical annotations during surgery. A digital image of a treatment site in a region of patient anatomy is captured using a camera and is displayed on an image display. The system displays an overlay marking an anatomic region of interest in the displayed image. During the course of the surgery, panning of the image results in the anatomic region of interest being outside the displayed field of view. In response to user input, the displayed image is subsequently panned such that the anatomic region of interest and the displayed overlay return to the displayed field of view.

4 Claims, 3 Drawing Sheets

(56) References Cited

U.S. PATENT DOCUMENTS

| | | | |
|---|---|---|---|
| 2016/0210435 A1* | 7/2016 | Neumann | G09B 23/288 |
| 2016/0225145 A1* | 8/2016 | Nagata | G06T 7/0012 |
| 2017/0273745 A1* | 9/2017 | Turquier | G16H 50/50 |
| 2017/0281031 A1* | 10/2017 | Houben | A61B 18/1492 |
| 2018/0133467 A1* | 5/2018 | Wald | A61N 1/086 |
| 2021/0015343 A1* | 1/2021 | Uyama | A61B 1/00048 |
| 2021/0145525 A1* | 5/2021 | Esposito | G06T 11/00 |
| 2021/0196398 A1* | 7/2021 | Ye | A61B 1/307 |
| 2021/0369463 A1* | 12/2021 | Toro Estrella | A61B 5/4504 |
| 2022/0070416 A1* | 3/2022 | Viering | G06T 7/33 |
| 2023/0038498 A1* | 2/2023 | Xu | A61B 34/30 |
| 2023/0225804 A1* | 7/2023 | Azizian | G06F 3/011 |
| | | | 715/771 |

* cited by examiner

CREATING SURGICAL ANNOTATIONS USING ANATOMY IDENTIFICATION

This application claims the benefit of U.S. Provisional Application No. 63/152,841, filed Feb. 23, 2021.

BACKGROUND

A surgeon viewing a display of a surgical site may which to annotate the display of surgical field for a variety of purposes.

An attending surgeon may annotate the surgical view as training for a surgical resident. A surgeon may annotate a video to document a procedure for conference presentations or other similar purposes. Annotation of a video may be helpful to assist with procedural planning. Annotation may also be used to identify or confirm the identify of certain portions of anatomy to assist with a supervised-autonomy or fully autonomous task or procedure.

DETAILED DESCRIPTION

A system useful for performing the disclosed methods may comprise a camera, a computing unit, a display, and, preferably, one or more user input devices.

The camera is one suitable for capturing images of the surgical site within a body cavity. It may be a 3D or 2D endoscopic or laparoscopic camera. Where it is desirable to use image data to detect anatomical structures in three dimensions, configurations allowing 3D data to be captured or derived are used (e.g. a stereo/3D camera, or a 2D camera with software and/or hardware configured to permit depth information to be determined or derived).

In embodiments used to generate annotations based on anatomy identified using computer vision, or to "attach" or associate user annotations with the locations of points/tissues captured in the image data, the computing unit is configured to receive the images/video from the camera. The computing unit is also configured to receive input from the user input device(s). The system may be one used in conjunction with a robot-assisted surgical system in which surgical instruments are maneuvered within the surgical space using one or more robotic components (e.g. robotic manipulators that move the instruments and/or camera, and/or robotic actuators that articulate joints, or cause bending, of the instrument or camera shaft.

An algorithm stored in memory accessible by the computing unit is executable to, depending on the particular application, use the image data to perform one or more of the functions described with respect to the described embodiments.

A variety of different types of user input devices may be used alone or in combination. Examples include, but are not limited to, eye tracking devices, head tracking devices, touch screen displays, mouse-type devices, voice input devices, foot pedals, or switches. Various movements of an input handle used to direct movement of a component of a surgical robotic system may be received as input (e.g. handle manipulation, joystick, finger wheel or knob, touch surface, button press). Another form of input may include manual or robotic manipulation of a surgical instrument having a tip or other part that is tracked using image processing methods when the system is in an input-delivering mode, so that it may function as a mouse, pointer and/or stylus when moved in the imaging field, etc. Input devices of the types listed are often used in combination with a second, confirmatory, form of input device allowing the user to enter or confirm (e.g. a switch, voice input device, button, icon to press on a touch screen, etc., as non-limiting examples).

Figure 1:
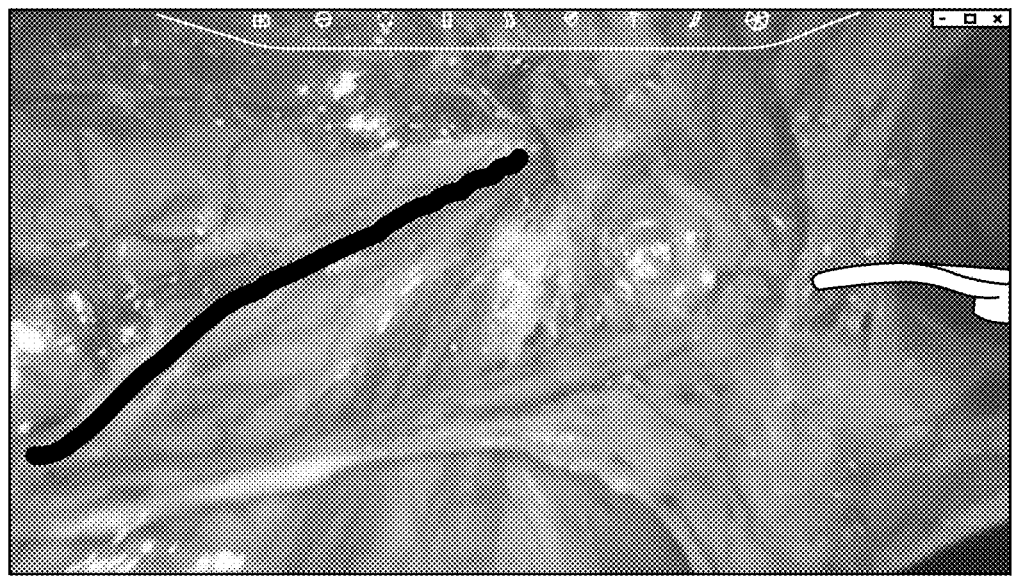
FIG. 1 shows an endoscopic display displaying a real-time image of a surgical site, with an overlay generated in response to annotation input provided by a user.
Figure 2:
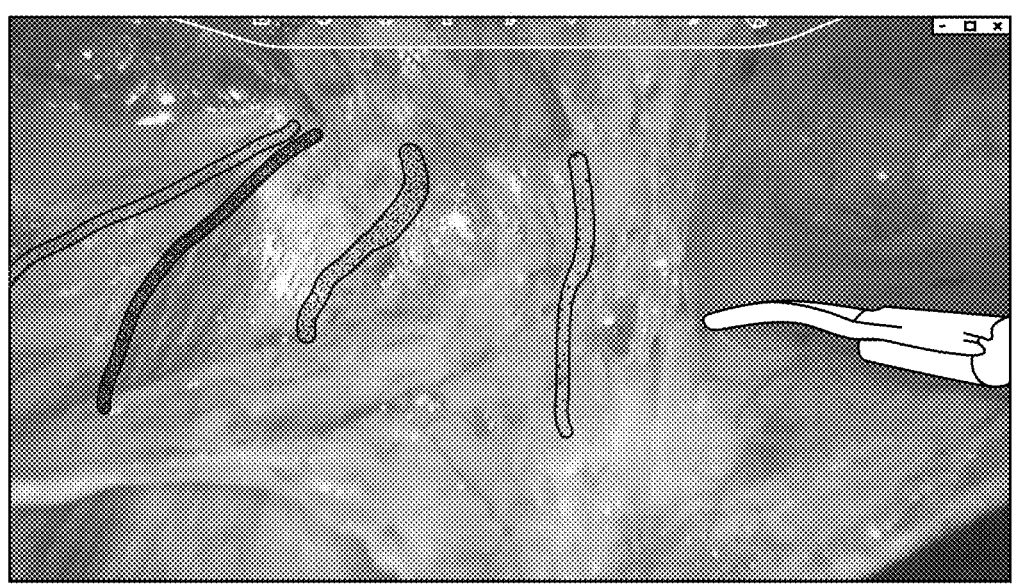
FIG. 2 is similar to FIG. 1, but shows four regions annotated using highlighting lines of different colors.

In a first embodiment depicted in FIGS. 1 and 2, digital annotations on the laparoscopic display are created using input from the user. For example, the user may use the input device or a touch screen tablet to electronically draw markings that are shown as overlays on the display (or a similar display on the tablet). In the drawings, the annotations appear as highlighting over the structures (e.g. ligaments, blood vessels, or other structures of interest) that the user wishes to keep track of. The system associates/attaches the markings to the location of the structures (as captured by the image data) that are marked. That way if the user pans the camera away from the marked areas (such that they are no longer on-screen), the annotations will again be displayed once the marked areas are again within the displayed field of view of the camera. In FIG. 2, four structures are marked, and the marked structures are each highlighted using different colored lines, with four lines in four difference colors shown in the second. The system may offer the user the ability to mark the areas using a variety of colors, shapes, patterns, etc.

Figure 3:
FIG. 3 shows an endoscopic display displaying a real-time image of a surgical site, with overlays marking anatomical features automatically identified by the system using computer vision techniques.

In other embodiments, the digital annotation may be created automatically, based on anatomy recognized in the surgical field by applying computer vision to the real time images of the surgical site. For example, in the FIG. 3 embodiment, the system automatically detects the infundibulopelvic ligament (commonly abbreviated IP ligament) and adds an overlay. The ureter is also automatically detected and marked with another overlay that functions as a "keep out" border to remind the user to avoid it when navigating instruments in the region. Overlays marking the inguinal canal and spermatic cord may likewise be displayed.

In some implementations, the annotations may be stored in a 3-dimensional model of the surgical scene and if the associated anatomy moves offscreen the overlay will be removed. In some cases, this overlay may be re-projected into the laparoscopic view once the endoscopic view moves into the same location. In some cases, the annotation may distort, "stretch" or morph to track the underlying anatomy. This may not be possible in all cases of large deformation, so the annotation may disappear once a certain distortion threshold is crossed.

This annotation may also naturally fade out over time.

In some implementations, the classification of structures may be highlighted in different colors.

This classification may also adjust system behavior. For instance, certain structures may have a warning or "no-fly" zone (optionally or automatically) attached to them.

In others, a structure that may be approached or needs to be cut during a certain procedure may be highlighted (e.g. in green).

Figure 4:
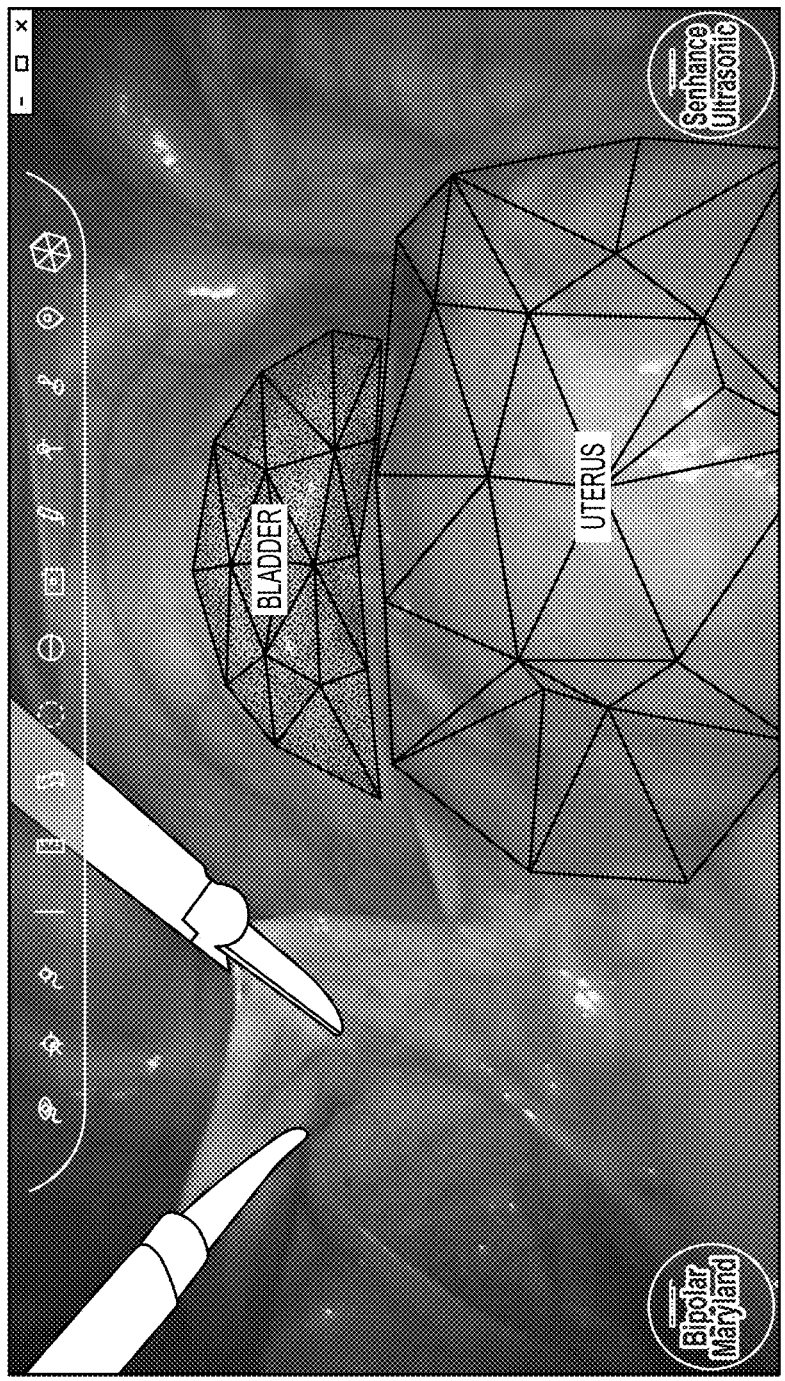
FIG. 4 shows an endoscopic display displaying a real-time image of a surgical site, with overlays marking organs automatically identified by the system using computer vision techniques. In this embodiment, the overlays utilize triangular grid patterns to convey 3D geometry and relative depth information.

FIG. 4 depicts overlays resulting from anatomy identification of organs. Here, geodesic mesh overlays are generated and displayed over the bladder and uterus following their detection.

In some anatomy ID configurations, the identification of the relevant anatomy is solely image based, and may be based on a single snapshot, and may be trained via machine learning/deep learning.

However, in these implementations, 3D stereo imaging can be employed to aid in further differentiation as well as the ability to extract 3D depth information along with the ability to use deep learning. In addition, as the image moves, it is possible to gain further information to define the boundaries of anatomy.

A surgical context model is also able to provide a spatial context for an anatomy identification application, incorporating knowledge about relevant adjacent anatomical structures as well as, in some cases, providing the view direction of the endoscope with respect to the body.

This aids in classification by eliminating anatomy from the classification that is likely currently invisible, as well as presenting the most likely visible anatomical structures to the recognition algorithm to enable a robust identification system.

Furthermore, the incorporation of the anatomical identification system with a robotic surgical system provides valuable kinematic information. This can be used to provide accurate mapping of endoscope view direction changes into a (continuously-updated) 3D model of the surgical site. In addition, this kinematic information can be used to differentiate between endoscope motion, motion of anatomy due to physiologic function, and motions of anatomy due to actions of the surgical instruments in the body cavity.

What is claimed is:

1. A method of marking and tracking anatomic features on an image display, comprising:
   capturing a digital image of a treatment site in a region of patient anatomy;
   displaying the digital image on an image display;
   receiving user input marking an anatomic region of interest on the image display;
   displaying an overlay marking the anatomic region of interest, said overlay comprising a three-dimensional geodesic mesh;
   causing the overlay to deform in response to deformation of tissue of the anatomic region of interest and, if deformation of the tissue crosses a predetermined distortion threshold, causing the overlay to disappear from the image display;
   in response to user input, panning the displayed image such that the anatomic region of interest is outside of the displayed field;
   in response to user input, panning the displayed image such that the anatomic region of interest and the displayed overlay returns to the displayed field.

2. The method of claim 1, wherein the anatomic region of interest is an organ.

3. The method of claim 2, wherein the organ is a bladder.

4. The method of claim 2 wherein the organ is a uterus.

* * * * *